(12) United States Patent
Patton et al.

(10) Patent No.: US 12,029,837 B2
(45) Date of Patent: Jul. 9, 2024

(54) FRAGRANCE DIFFUSING DEVICE AND CARTRIDGE

(71) Applicant: AROME D'ART, Costa Mesa, CA (US)

(72) Inventors: Douglas Patton, Costa Mesa, CA (US); Jeffrey Thompson, Irvine, CA (US)

(73) Assignee: AROME D'ART, Newport Beach, CA (US)

( * ) Notice: Subject to any disclaimer, the term of this patent is extended or adjusted under 35 U.S.C. 154(b) by 721 days.

(21) Appl. No.: 17/055,965

(22) PCT Filed: Feb. 20, 2019

(86) PCT No.: PCT/US2019/018827
§ 371 (c)(1),
(2) Date: Nov. 16, 2020

(87) PCT Pub. No.: WO2019/164989
PCT Pub. Date: Aug. 29, 2019

(65) Prior Publication Data
US 2021/0379230 A1    Dec. 9, 2021

Related U.S. Application Data

(60) Provisional application No. 62/743,497, filed on Oct. 9, 2018, provisional application No. 62/632,715, filed on Feb. 20, 2018.

(51) Int. Cl.
*A61L 9/12*    (2006.01)
(52) U.S. Cl.
CPC ......... *A61L 9/122* (2013.01); *A61L 2209/133* (2013.01); *A61L 2209/15* (2013.01)

(58) Field of Classification Search
None
See application file for complete search history.

(56) References Cited

U.S. PATENT DOCUMENTS

| 2004/0009103 A1 | 1/2004 | Westring |
| 2010/0243754 A1 | 9/2010 | Harris |

(Continued)

FOREIGN PATENT DOCUMENTS

| CN | 1798584 A | 7/2006 |
| CN | 102177075 B | 2/2013 |

(Continued)

OTHER PUBLICATIONS

European Patent Office, European Search Report, Feb. 3, 2022.

(Continued)

*Primary Examiner* — Jelitza M Perez
(74) *Attorney, Agent, or Firm* — Ryan Dean; Umberg Zipser LLP (57) ABSTRACT

Various embodiments of diffusing devices and scent cartridges are described. The diffusing device can include a cover or retaining ring that magnetically attaches to the diffusing device to hold the cartridge in place. The scent cartridge can include a top plate suspended above the cartridge such that a scent depository of the cartridge is hidden or obscured while the top plate can include artwork or a kinetic arrangement that has a change in visual appearance due to an airflow against or through the top plate.

18 Claims, 13 Drawing Sheets

(56) References Cited

U.S. PATENT DOCUMENTS

2011/0132907 A1\* 6/2011 Hajichristou ...... B65D 43/0225
                                                    215/337
2013/0049236 A1   2/2013 Garon et al.
2017/0253338 A1   9/2017 Fantuzzi et al.

FOREIGN PATENT DOCUMENTS

CN    104596064 A    5/2015
EP      2334571 B1  10/2012
WO    2010018431 A1  2/2010

OTHER PUBLICATIONS

China Patent Office, Second Office Action, Jul. 29, 2022.
Korean Intellectual Property Office, International Search Report and Written Opinion, Jul. 26, 2019.
China Patent Office, First Office Action, Dec. 13, 2021.

\* cited by examiner

FRAGRANCE DIFFUSING DEVICE AND CARTRIDGE

This application is a national phase (§ 371) application of PCT application no. PCT/US19/18827 filed on Feb. 20, 2019, which itself claims priority to U.S. provisional application having Ser. No. 62/632,715 filed on Feb. 20, 2018 and U.S. provisional application having Ser. No. 62/743,497 filed on Oct. 9, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is fragrance diffusing devices.

BACKGROUND

The following description includes information that may be useful in understanding the present invention. It is not an admission that any of the information provided herein is prior art or relevant to the presently claimed invention, or that any publication specifically or implicitly referenced is prior art.

In general, fragrance diffusing devices include a base unit and a cartridge that attaches to the base unit. A fragrance often in liquid form is then wicked or otherwise pulled from the cartridge, such that the fragrance passes through the base unit before exiting the device. Such devices are problematic as they retain previous scent(s) even when a different cartridge is used, they fail to diffuse the scent circumferential from the device, and are often eyesores that people attempt to hide by placing them in locations where such fragrance takes longer to reach the preferred location.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for improved diffusing devices and cartridges that address the above-identified problems.

SUMMARY OF THE INVENTION

The inventive subject matter provides apparatus, systems and methods for fragrance dispensing units and cartridges that can be used together to disperse a fragrance from the cartridge to an area surrounding the dispensing unit.

Contemplated dispensing units can include a having lower and upper surfaces, wherein the base includes a fan and power source configured to power the fan. A first set of magnets can be disposed at or beneath the upper surface of the base.

The unit can further include a cover having lower and upper surfaces, where the lower surface comprises a second set of magnets having a polarity that is opposite of the first set of magnets such that the cover is magnetically attached to the base via a magnetic coupling between the first and second sets of magnets.

The base or cover can include a third set of magnets. Where the third set of magnets is disposed at or beneath the upper surface of the base, the third set of magnets have a polarity that is the same as that of the second set of magnets. Where the cover comprises the third set of magnets, the third set of magnets have a polarity that is the same as that of the first set of magnets. In either case, by rotating the cover with respect to the base, the magnetic coupling changes to a repulsive force assisting in removing the cover from the base.

The base can include a recessed central portion surrounded by an exterior wall that forms the upper surface of the base, where the recessed central portion is configured to receive a cartridge.

The scent cartridge can be disposed on the recessed portion of the base, and thereby be disposed adjacent to and above the fan in the base. Contemplated scent cartridge can include a fragrance depository where the scent or fragrance is stored before being dispersed. In preferred embodiments, the fragrance depository comprises a plurality of scented beads that evaporate over time depending upon airflow. However, the fragrance depository could alternatively comprise a gel or liquid that is stored within the housing. Contemplated scented beads include ethylene-vinyl acetate (EVA) beads that have previously absorbed one or more scented solutions.

It is contemplated that the scent cartridge can include a top plate suspended above the upper surface of the cartridge by a post that extends upwardly from the cartridge to the plate. The top plate advantageously can include an artwork or kinetic arrangement while also hiding the scent depository beneath the top plate. In addition, the top plate can divert air and cause air to flow circumferentially from the cartridge.

Advantageously, because scented air flows from the scent depository and then exits the cartridge, scented air does not flow through the base. Therefore, when the cartridge is replaced and a new cartridge used, there is unlikely to be any remaining portion of the prior scent on the base.

Various objects, features, aspects and advantages of the inventive subject matter will become more apparent from the following detailed description of preferred embodiments, along with the accompanying drawing figures in which like numerals represent like components.

DETAILED DESCRIPTION

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
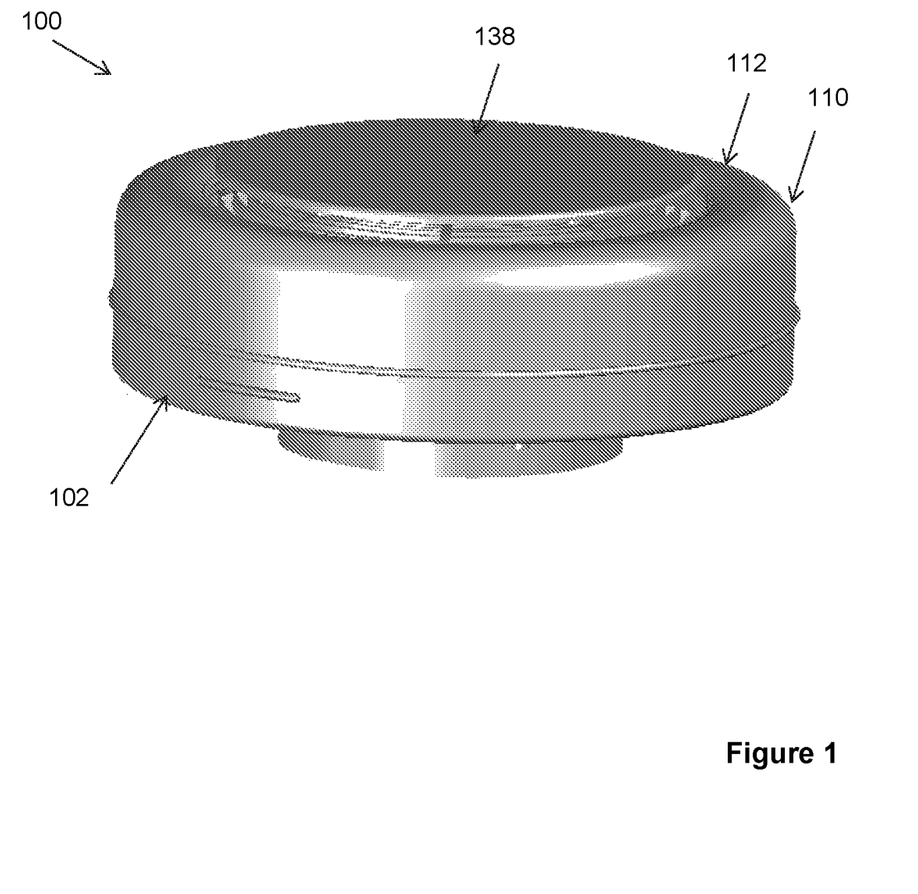
FIG. 1 is a perspective view of one embodiment of the device.
Figure 2:
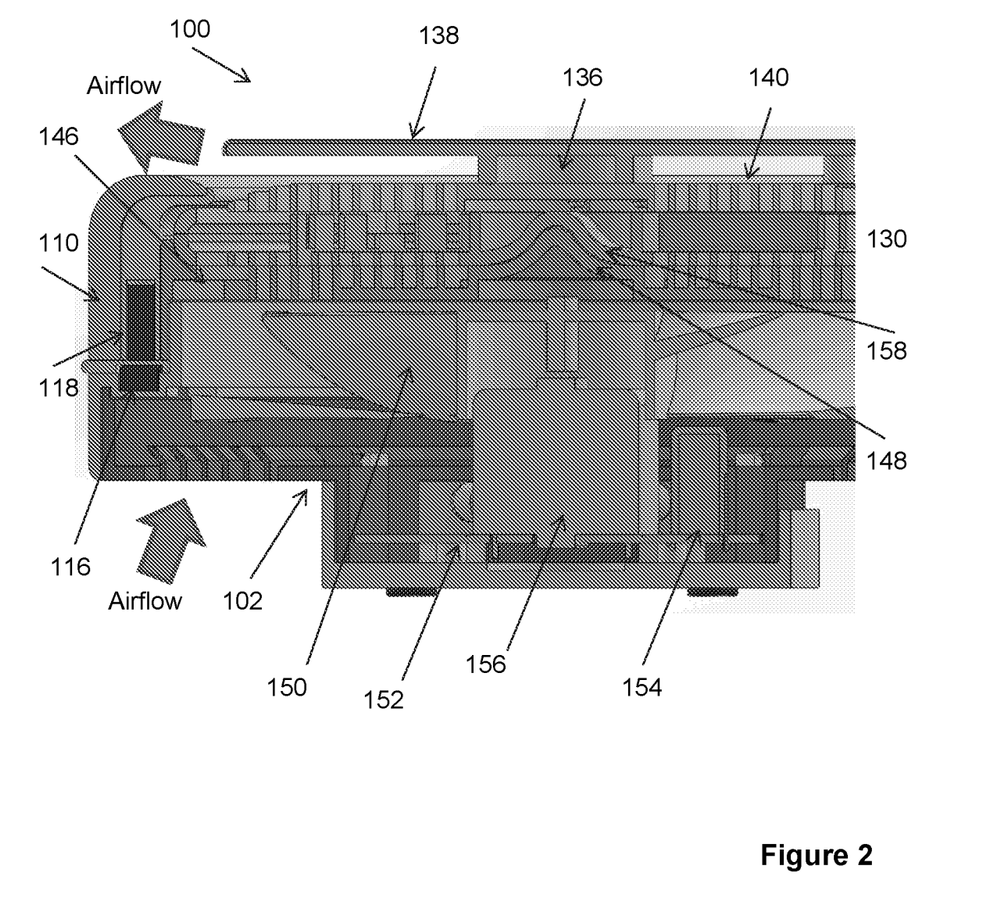
FIG. 2 is a vertical, cross-section view of the device of FIG. 1.
Figure 3:
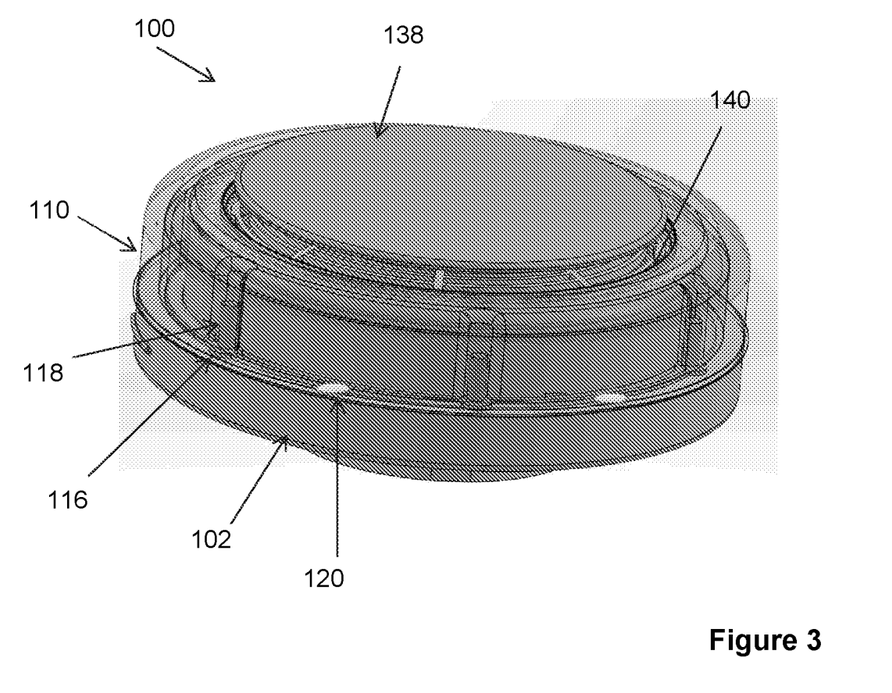
FIG. 3 is another perspective view of the device of FIG. 1.
Figure 4:
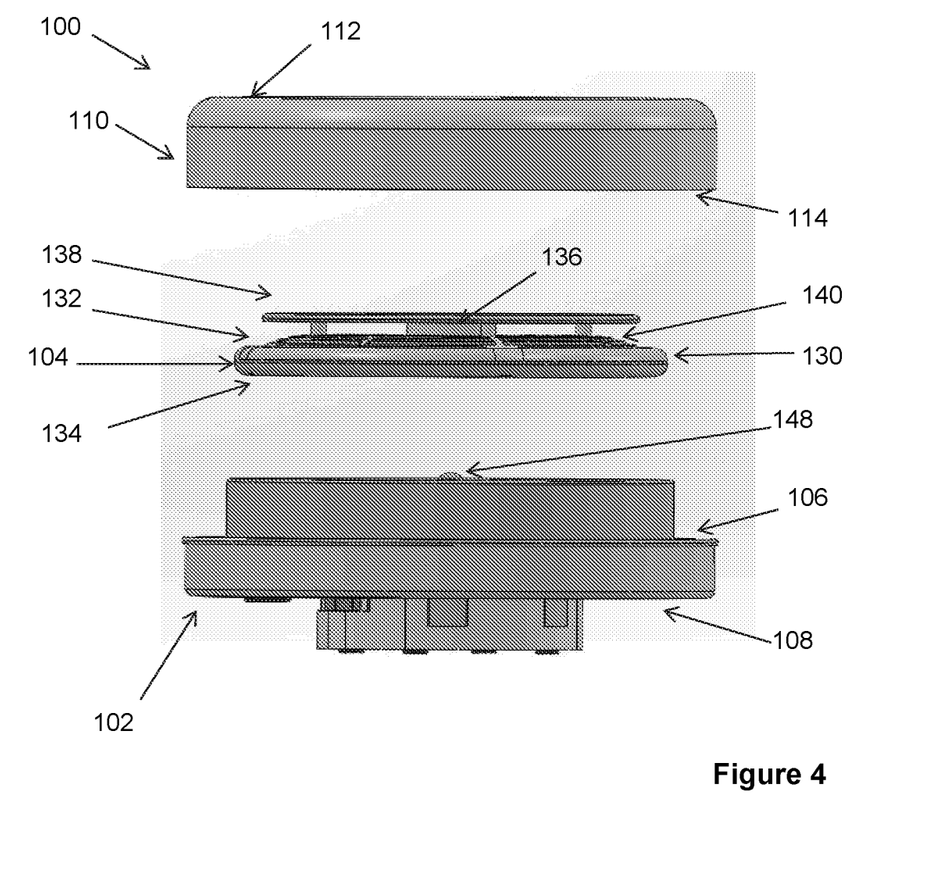
FIGS. 4-6 are various exploded views of the device of FIG. 1.
Figure 5:
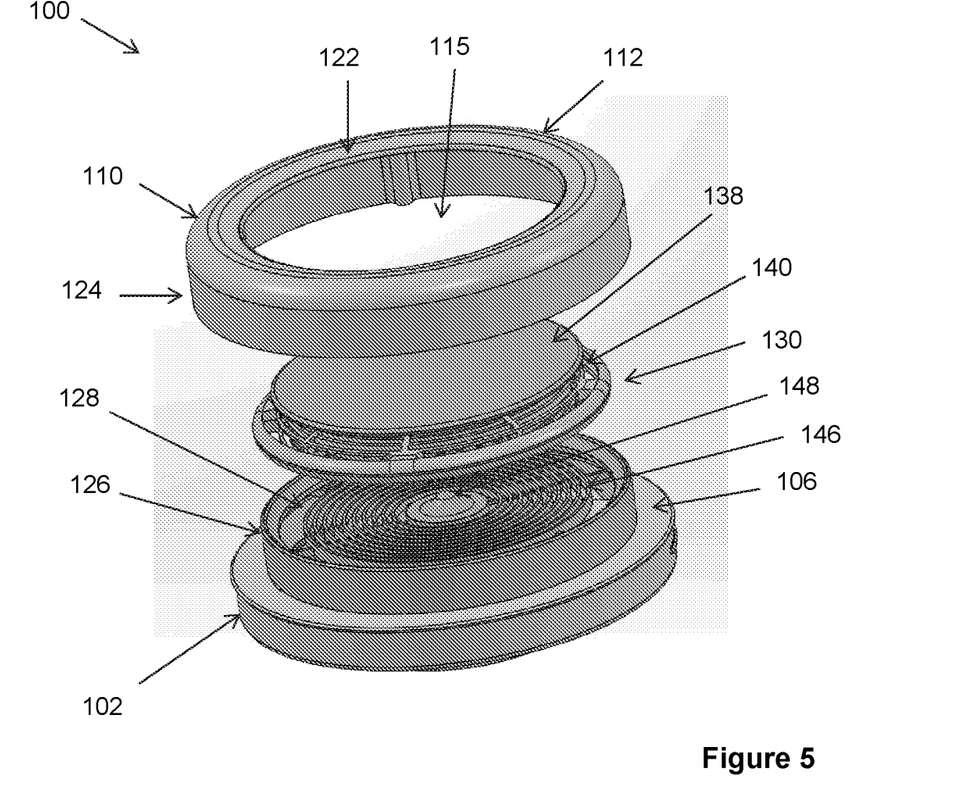
Figure 6:
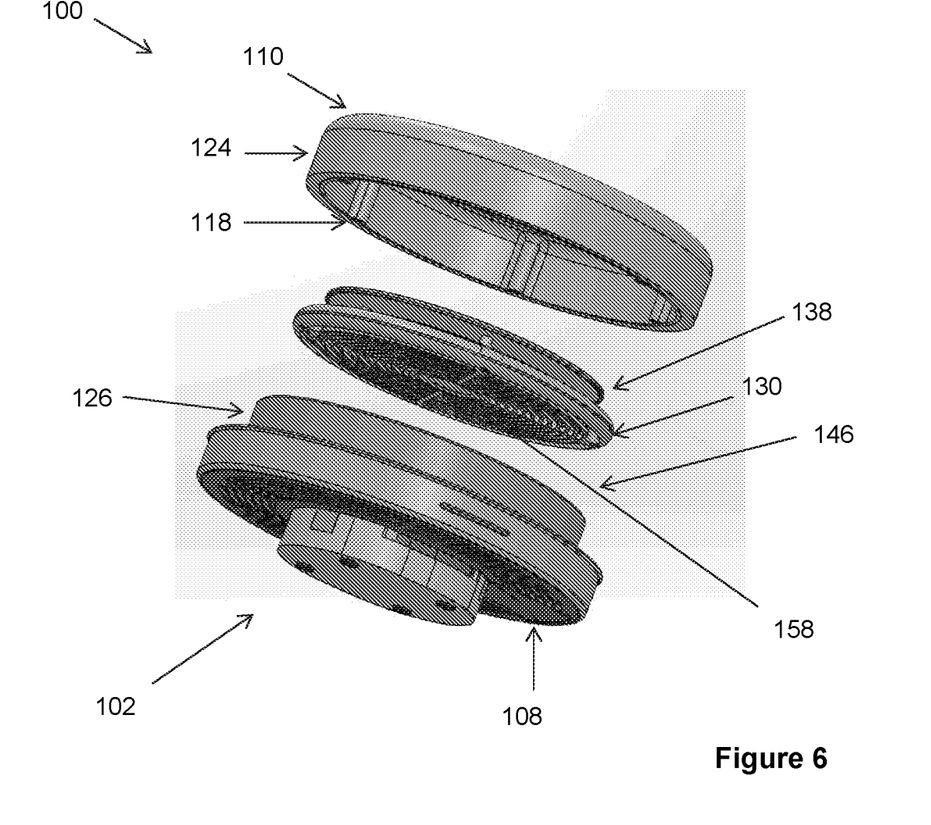
Figure 7:
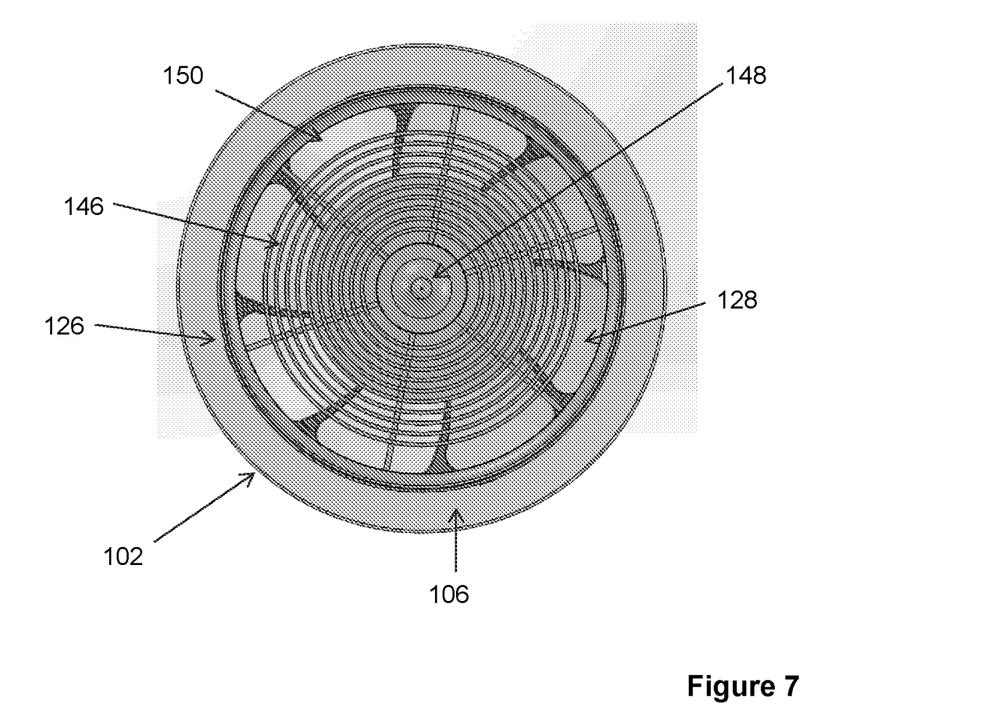
FIG. 7 is a top view of one embodiment of a base unit.
Figure 8:
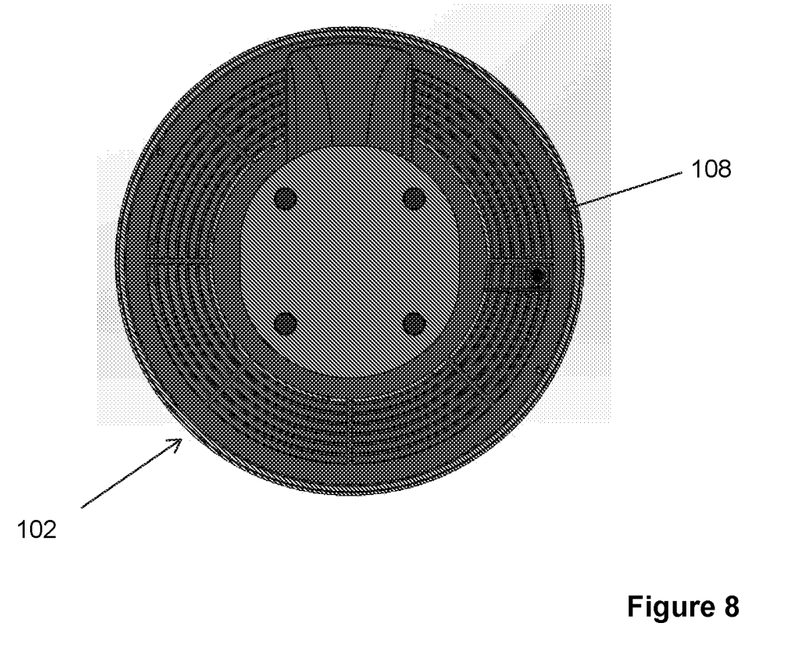
FIG. 8 is a bottom view of the base unit of FIG. 7.
Figure 9:
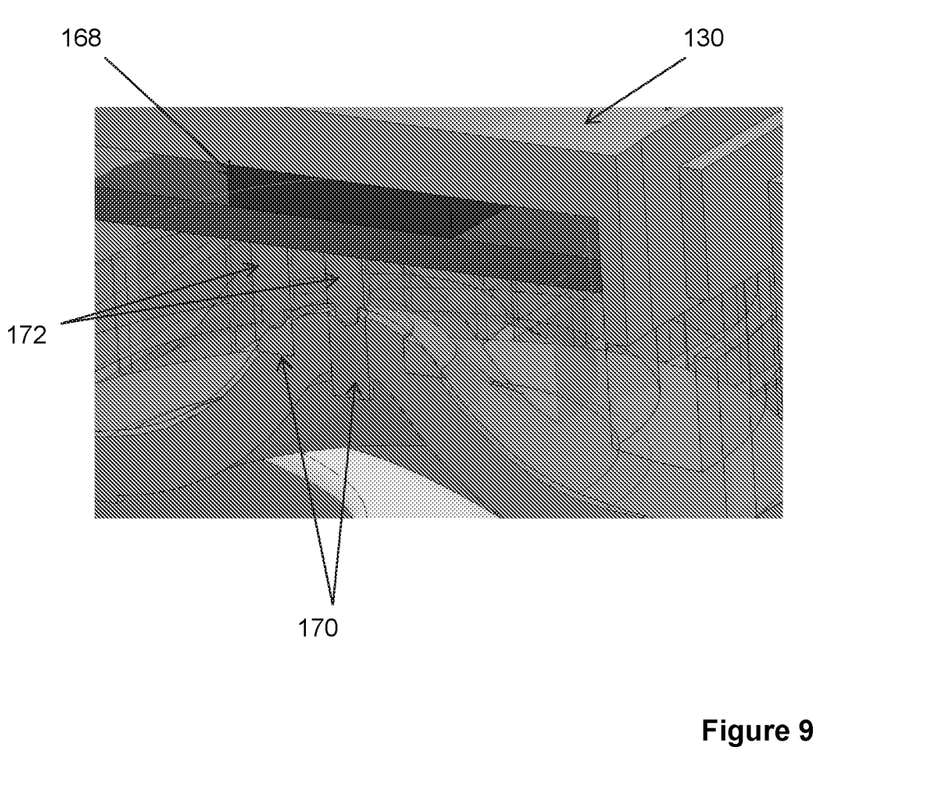
FIG. 9 is an enlarged, cross-section view of the device of FIG. 1.

FIGS. 1-2 illustrates one embodiment of a fragrance dispensing unit 100 having a scent cartridge 130 disposed within the unit 100. The unit 100 comprises a base 102 and a cover or ring 110 is magnetically coupled to the base 102, and that collectively maintain the scent cartridge 130 within the unit 100.

The base 102 comprises an upper surface 106 and a lower surface 108. Within the base 102 is disposed a fan 150, which is connected to a motor 156 that drives the fan 150. The base can also include electronics 152 that control the motor 156 and thereby can vary the fan speed or turn the fan 150 on or off. A battery 154 can be included for power storage and to power the various components of the base 102. Alternatively or additionally, the base 102 can be coupled to a line voltage to charge the battery 154 and/or power the unit 100. In some embodiments, the battery 154 can be charged via induction.

The base 102 can include a grill 146 disposed above the fan 150, and that includes a plurality of apertures through which air can flow from the fan and through the grill 146. In this manner, air can flow through the lower surface 108 of the base 102 as shown by arrow past the fan 150 and through the grill 146.

A first set of magnets 116 can be disposed at or beneath the upper surface 106 of the base 102, such that each of the magnets has the same polarity in the portion of the magnet nearest the upper surface 106. Thus, for example, where each magnet has a north and south pole end, all of the magnets 116 of the first set will have the same end facing toward the upper surface 106.

A second set of magnets 118 can be disposed at or above the lower surface 114 of the cover 110, such that each of the magnets has the same polarity in the portion of the magnet nearest the lower surface 114. It is especially preferred that the polarity of the second set of magnets 118 is opposite the polarity of the first set of magnets 116. In this manner, the magnetic attraction between the first and second sets of magnets 116, 118 can couple the cover 110 to the base 102.

In some contemplated embodiments, the base 102 can comprise a third set of magnets 120 disposed at or beneath the upper surface 106 of the base 102. In such embodiments, the third set of magnets 120 each has the same polarity in the portion of the magnet nearest the upper surface 106 and that polarity is opposite of the first set of magnets 116 and the same as the second set of magnets 118. In this manner, when the cover 110 is coupled with the base 102 and rotated with respect to the base 102, the third set of magnets 120 and the second set of magnets 118 will create a repulsive force due to the same polarity of the magnets, which will facilitate removal of the cover 110 from the base 102.

In other contemplated embodiments, the cover 110 can comprise a third set of magnets 120 disposed at or above the lower surface 114 of the cover 110. In such embodiments, the third set of magnets 120 each has the same polarity in the portion of the magnet nearest the lower surface 114 and that polarity is opposite of the second set of magnets 118 and the same as the first set of magnets 116. In this manner, when the cover 110 is coupled with the base 102 and rotated with respect to the base 102, the third set of magnets 120 and the first set of magnets 116 will create a repulsive force due to the same polarity of the magnets, which will facilitate removal of the cover 110 from the base 102.

When the cover 110 is coupled with the base 102, a lower surface 114 of the cover 110 abuts or rests on the upper surface 106 of the base 102. The cover 110 can also include a rim 122 that defines an upper surface 112 of the cover 110. The rim extends inwardly from a wall 124 of the cover 110.

The unit 100 can comprise a scent cartridge 130 that is preferably disposable and removable from the base 102. The scent cartridge 130 has an upper surface 132 and a lower surface 134, with the upper and lower surfaces 132, 134 each having one or more apertures to permit air to flow through the cartridge from the fan 150, for example.

The scent cartridge 130 can include a post 136 extending upwardly from the upper surface 132, and that supports a top plate 138 that is suspended above the scent cartridge 130. In this manner, a first end of the post 136 can be attached to the scent cartridge 130, and the second opposing end of the post 136 can be attached to the top plate 138. The top plate 138 preferably is sized and dimensioned to cover or obscure all or a portion of the cartridge 130. Advantageously, the top plate 138 can cause some or all of the airflow to be directed circumferentially from the base 102 and cartridge 130, rather than simply directed upwardly as in many prior art devices. This helps to ensure an even scent distribution in a room, for example, from the cartridge 130.

Figure 10:
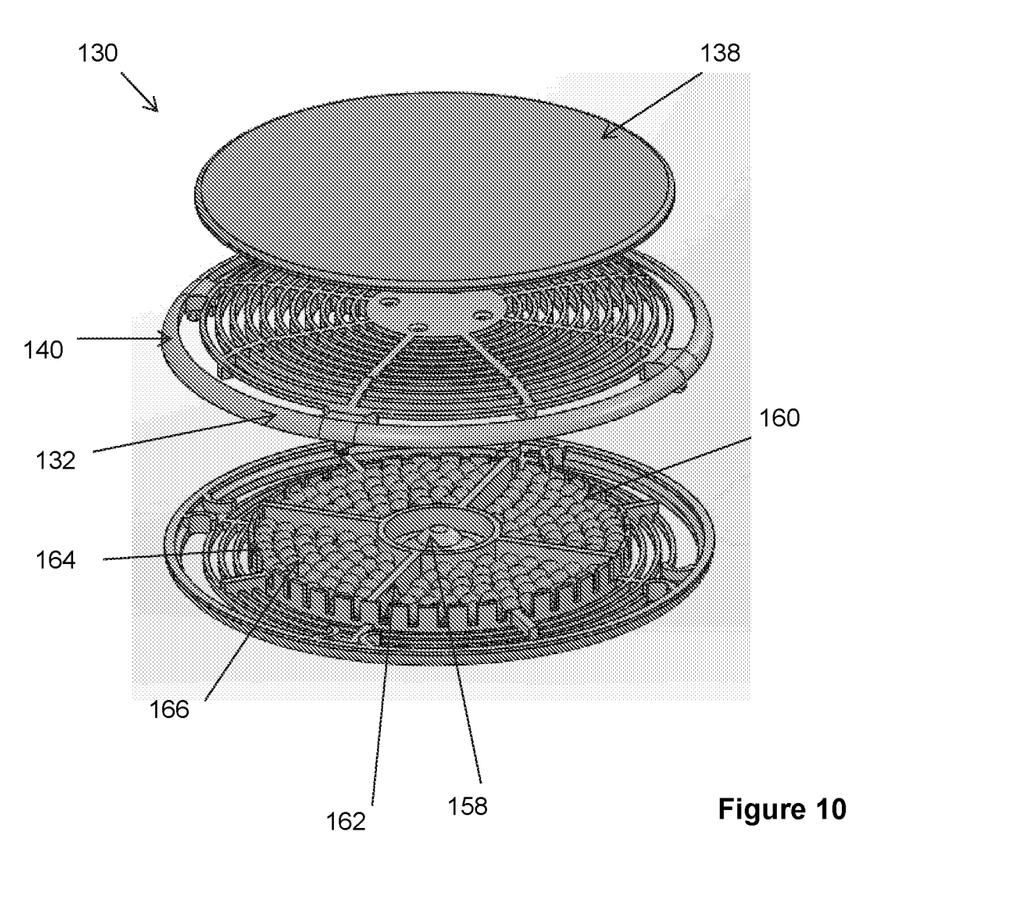
FIG. 10 is an exploded view of one embodiment of a scent cartridge.

The cartridge 130 can further include a grill 140 disposed above a scent repository 160 in the cartridge 130. The grill 140 ensures the scent repository 160 is not disturbed or that the beads 166 or other scented pieces are not removed from the cartridge 130. As shown, the scent repository 160 preferably comprises a one or more quadrants 164 (here, four quadrants), which each contains scented beads 166. Contemplated scented beads 166 include those formed from ethylene-vinyl acetate. However, in other embodiments, a scented gel or liquid could be disposed within the scent depository 160. The quadrants 164 can be formed by one or more walls 162 within the scent depository 160.

Figure 11:
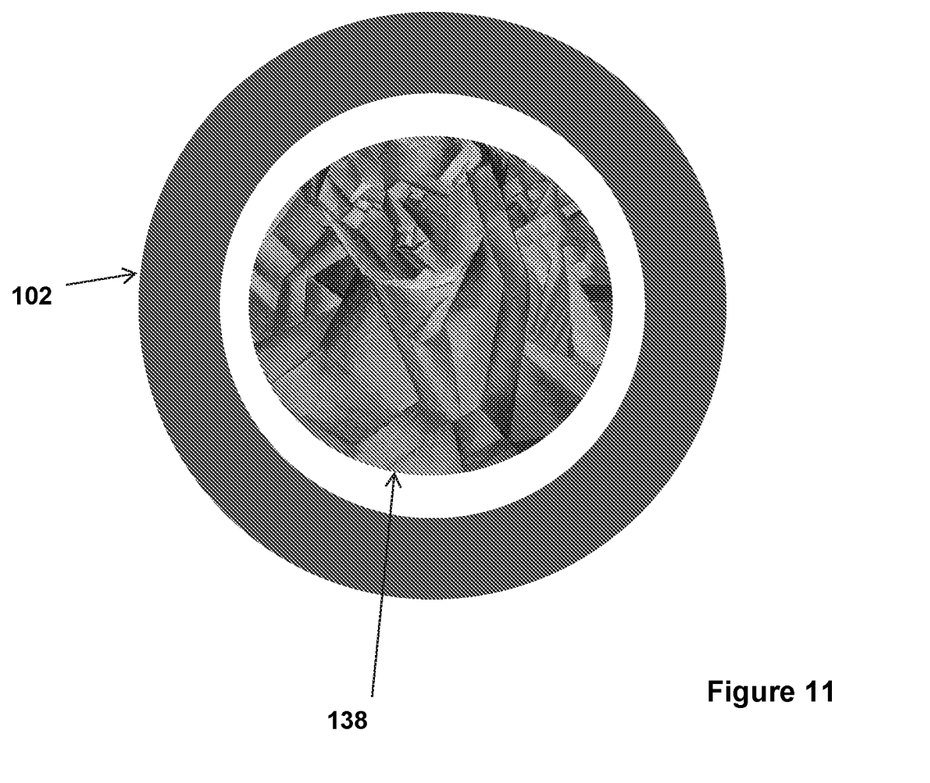
FIGS. 11-13 are top views of various embodiments of top plates for a scent cartridge.
Figure 12:
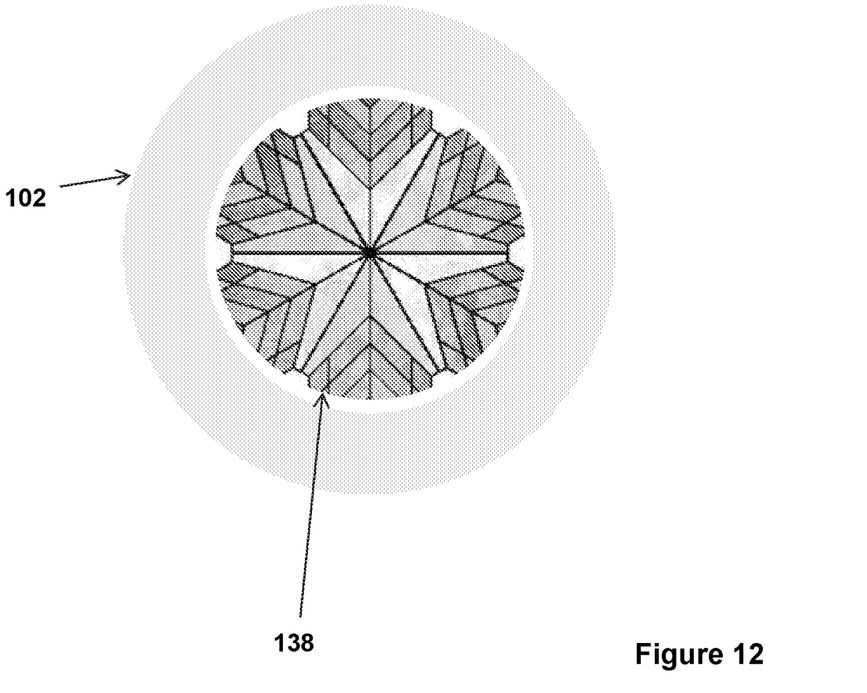

As shown in FIGS. 11-12, the top plate 138 can comprise an artwork which could include an image or a transparent or translucent portion(s) such as the stained glass replica shown in FIG. 12.

Figure 13:
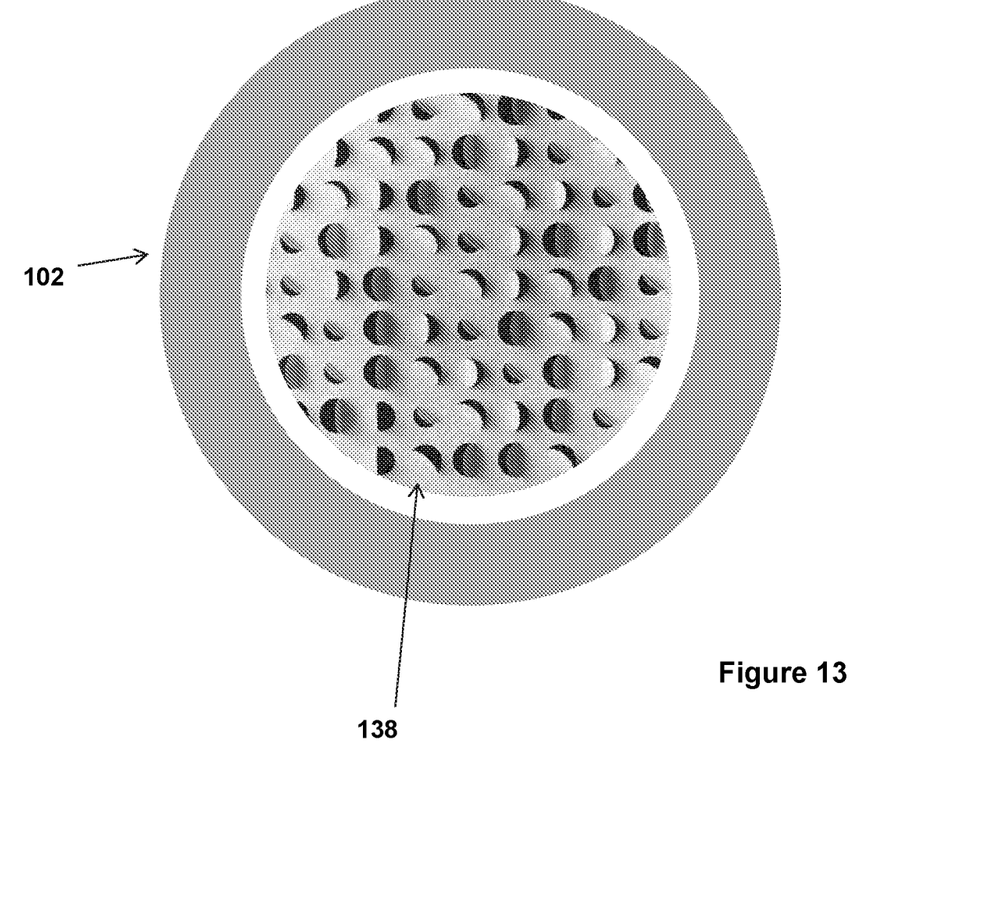

Alternatively, as shown in FIG. 13, the top plate 138 can comprise a kinetic arrangement or sculpture, which itself can change in visual appearance based on airflow passing through the kinetic arrangement or contacting a lower surface thereof. For example, the top plate can include a pressed-paper portion that can animate/flutter when the fan is in use.

The scent cartridge 130 preferably rests within a recessed area 128 of the base 102 formed at least partially by wall 126. The recessed area 128 can include a dimple or other projection 148. When the cartridge is positioned within the recessed area 128, the projection 148 is inserted into a recess 158 on the cartridge 130. This helps ensure proper placement of the cartridge 130 within the recessed area 128. The recessed area 128 is disposed above the fan 150.

Once the cartridge 130 is inserted within the recessed area 128 of base 102, the cover or ring 110 can be placed on an upper surface 132 of the cartridge 130, such that rim 122 of the cover 110 rests on the upper surface 132 of the cartridge and keeps the cartridge 130 within the recessed area 128. In such embodiments, it is contemplated that an upper surface 132 of the scent cartridge 130 is flush with an upper surface of the wall 126. Thus, a diameter of the rim 122 is less than a diameter of the cartridge 130.

The upper surface 112 of the cover 110 can include an aperture 115 defined by the rim 122. In this manner, when the cover 110 is attached to the base 102, the post of the cartridge 130 extends through the aperture 115 and the top plate 138 will extend above the cover 110.

When the fan 150 is turned on, air enters through a lower surface 108 of the base 102, past the fan 150, through the grill 146 of the base 102. From there, the non-scented air enters the scent cartridge 130 through its lower surface 134, passes through the scent depository 160, and exists through grill 140 of the cartridge 130. The now scented air exits through the space between the grill 140 and the top plate 138. As discussed above, the top plate 138 advantageously can cause the scented air to disperse circumferentially from the cartridge 130. In this manner, scented air flows from the scent cartridge 130 and out of the device 100 without passing through the base unit 102. Thus, little to no residual fragrance will be left on base 102 when the cartridge 130 is removed from the base 102, as the change in fragrance cartridge 130 will change the grill 140 through which the scented air passes so that different scents are not mixed.

In some embodiments, the cartridge 130 can include one or more light sources. It is contemplated that the light sources can be configured to illuminate during specific times of day either through a timer, a direct on/off control, or a signal received by an ambient light sensor. Where the top plate comprises a transparent or translucent portion, the light source can add to the visual effect of the top plate's artwork or kinetic arrangement.

It is contemplated that the electronics 152 can be configured to monitor a lifespan of the cartridge 130. Preferably, both the cartridge 130 and the base unit 102 have electrical contacts that contact one another when the cartridge 130 is placed on to the base unit 102, such as described above. In one embodiment, the dimple or other projection 148 could include an electrical contact 170 that contacts an electrical contact 172 disposed in recess 158 of the cartridge 130.

For example, when a cartridge 130 is first inserted into the base unit 102, the electronics can begin a timer that indicates how long the cartridge 130 has been inserted into the base unit 102. Via the electrical connection between the cartridge 130 and the base unit 102, the electronics could receive information about the cartridge, such as the type of cartridge 130 and some code, indicia or other means to indicate that the cartridge 130 is authentic and not a knock off cartridge. The information could also include a serial number or other unique identifier to prevent reuse of the cartridge 130 and to ensure that if the same cartridge is removed and reinserted, the timer does not reset.

The electronics 152 can comprise a processor, a memory with stored algorithms, and a PCB with other components. One of the stored algorithms can calculate a current lifespan of the cartridge 130 by calculating the amount of time the cartridge 130 has been open and inserted into the base 102, and the amount of time the fan 150 has been on while the cartridge 130 has been inserted within the base 102. Based on known evaporation rates of the scented beads 166 or other items in the scent depository 160, the electronics 152 can multiply the evaporation rate of the scented beads 166 by the time the cartridge has been inserted but the fan 150 off, as well as the evaporation rate of the scented beads 166 by the time the cartridge has been inserted and the fan 150 on. Adding these two values will allow the electronics 152 to determine the remaining percentage or amount of scent available in the cartridge 130.

Some of the information such as evaporation rates and total amount of scent of the cartridge 130 could be stored in the cartridge 130 and transferred to the base 102, transferred to the base from a remote source, or stored in the base 102. This is important as different cartridges may have different evaporation rates.

It is contemplated that the base 102 can include a transceiver on the electronics 152, for example, configured to transmit and receive information from a remote source such as a smart phone or other portable computing device. Thus, for example, the base 102 could transmit a remaining life of the cartridge to a user. In some embodiments, the user could control operation of the base 102 from the portable computing device. In other embodiments, the base 102 could transmit information to a user's device that can load a website, an image, or story that relates to the cartridge that was installed in the device 100.

In other contemplated embodiments, the cartridge 130 can include a memory and/or a microchip 168, which can be used to control fan speed in relation to scent aroma, for example. In addition, the microchip 168, or the electronics 152 of the base 102 can illuminate a light when the scent is expended. The electronics 152 and/or microchip 168 of the cartridge 130 can help to prevent the base 102 from working if a knockoff scent cartridge is being used.

It is further contemplated that the device 100 can be turned on/off by simply touching an annual ring or other portion of the base 102. This can allow powering on or off via capacitance. In addition, a bottom of the base 102 can have a slot to attach the base 102 to a mount or other support. In the slot can be a positive/negative connection so the mount or other support can transmit power to the base 102.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A fragrance dispensing unit, comprising:
   a base having lower and upper surfaces, wherein the base includes a fan and power source configured to power the fan, and wherein the base comprises a recessed central portion surrounded by an exterior wall that forms the upper surface of the base, and wherein the recessed central portion is disposed above the fan;
   a scent cartridge configured to be inserted within the recessed central portion of the base, wherein the scent cartridge comprises a top plate suspended above the upper surface of the scent cartridge by a post that extends upwardly away from the scent cartridge to the top plate, and wherein the top plate causes air flowing from the scent cartridge to be circumferentially dispersed from the scent cartridge;
   a first set of magnets disposed at or beneath the upper surface of the base;
   a cover having lower and upper surfaces, wherein the lower surface of the cover comprises a second set of magnets having a polarity that is opposite of the first set of magnets such that the cover is magnetically attached to the base;
   a third set of magnets disposed either (i) at or beneath the upper surface of the base and having a polarity that is the same as that of the second set of magnets, or (ii) at or above the lower surface of the cover and having a polarity that is the same as that of the first set of magnets, such that rotation of the cover with respect to the base when the cover is attached to the base causes the cover to be repelled from the base due to the same polarity of the third set of magnets with either the first or second set of magnets.

2. The fragrance dispensing unit of claim 1, wherein the third set of magnets are disposed at or beneath the upper surface of the base, and wherein the third set of magnets have a polarity that is the same as that of the second set of magnets, such that rotation of the cover with respect to the base when the cover is magnetically attached to the base causes the cover to be repelled from the base due to the polarity of the second and third set of magnets being the same.

3. The fragrance dispensing unit of claim 1, wherein the third set of magnets are disposed at or above the lower surface of the cover, and wherein the third set of magnets have a polarity that is the same as that of the first set of magnets, such that rotation of the cover with respect to the base when the cover is magnetically attached to the base causes the cover to be repelled from the base due to the polarity of the first and third set of magnets being the same.

4. The fragrance dispensing unit of claim 1, wherein the cover comprises an aperture on the upper surface, and a rim that extends inwardly from an outer surface of the cover.

5. The fragrance dispensing unit of claim 1, wherein the recessed central portion comprises a projection or dimple that extends upwardly from the base.

6. The fragrance dispensing unit of claim 5, wherein the scent cartridge comprises a recessed area configured to receive the projection or dimple.

7. The fragrance dispending unit of claim 6, wherein the cover abuts the upper surfaces of the scent cartridge and base when the cover is magnetically attached to the base.

8. The fragrance dispensing unit of claim 1, wherein the top plate is sized and dimensioned to cover the scent cartridge.

9. The fragrance dispensing unit of claim 1, wherein the top plate comprises a kinetic arrangement such that air flow through or against the top plate causes movement of the kinetic arrangement and generates a visual change of the look of the top plate.

10. The fragrance dispensing unit of claim 1, wherein scent cartridge comprises a light source, and wherein the light source causes a visual change in a kinetic arrangement or artwork disposed on the top plate.

11. The fragrance dispensing unit of claim 1, wherein the fan in the base is configured to cause airflow through the scent cartridge such that scented air flows from the scent cartridge without passing through the base.

12. The fragrance dispensing unit of claim 6, wherein the scent cartridge comprises an electrical interface that contacts an electrical interface of the base when the scent cartridge is installed in the recessed central portion of the base.

13. The fragrance dispensing unit of claim 6, wherein the base comprises electronics configured to calculate a status of the scent cartridge, and wherein the electronics are configured to receive information about the scent cartridge, and wherein the status comprises an amount or percentage of a remaining scent that can be dispersed from the scent cartridge.

14. A fragrance dispensing unit, comprising:
- a base having lower and upper surfaces, wherein the base includes a fan and power source configured to power the fan;
- a first set of magnets disposed at or beneath the upper surface of the base;
- a cover having lower and upper surfaces, wherein the lower surface of the cover comprises a second set of magnets having a polarity that is opposite of the first set of magnets such that the cover is magnetically attached to the base;
- a third set of magnets disposed either (i) at or beneath the upper surface of the base and having a polarity that is the same as that of the second set of magnets, or (ii) at or above the lower surface of the cover and having a polarity that is the same as that of the first set of magnets, such that rotation of the cover with respect to the base when the cover is attached to the base causes the cover to be repelled from the base due to the same polarity of the third set of magnets with either the first or second set of magnets;
- a scent cartridge configured to be inserted within a recessed central portion of the base, and wherein the scent cartridge comprises a recessed area configured to receive a projection or dimple;
- wherein the base comprises electronics configured to calculate a status of the scent cartridge, and wherein the electronics are configured to receive information about the scent cartridge, and wherein the status comprises an amount or percentage of a remaining scent that can be dispersed from the scent cartridge; and
- wherein the electronics calculate the status based on (i) an evaporation rate of a scent deposit within the scent cartridge when the fan is on, (ii) an evaporation rate of a scent deposit within the scent cartridge when the fan is off, (iii) an amount of time the fan has been on since the scent cartridge was first contacted to the base, and (iv) an amount of time the fan has been off since the scent cartridge was first contacted to the base.

15. The fragrance dispensing unit of claim 1, wherein the cover comprises an aperture on the upper surface, and a rim that extends inwardly from an outer surface of the cover, and wherein the top plate of the scent cartridge extends above the aperture, and wherein the rim abuts an upper surface of the scent cartridge.

16. The fragrance dispensing unit of claim 4, wherein the top plate of the cartridge extends through and above the aperture, and wherein the rim abuts an upper surface of the cartridge.

17. The fragrance dispensing unit of claim 1, wherein the scent cartridge and top plate form a single component that is removable from the base.

18. The fragrance dispensing unit of claim 1, wherein the fan causes air to flow through the scent cartridge such that the air flows upwardly from the scent cartridge, and wherein the top plate causes the air flowing from the scent cartridge to be circumferentially dispersed from the scent cartridge as the air contacts the top plate.

* * * * *